United States Patent [19]
Freeman

[11] Patent Number: 6,103,951
[45] Date of Patent: Aug. 15, 2000

[54] RELEASABLE WOUND DRESSING FOR EFFICIENT REMOVAL OF EXUDED FLUID

[76] Inventor: Frank Freeman, Ekali, Hope Town Elbow Cay Island, Abaco, Bahamas

[21] Appl. No.: 09/170,558

[22] Filed: Oct. 13, 1998

[51] Int. Cl.$^7$ ..................................................... A61F 13/00
[52] U.S. Cl. .................................. 602/48; 602/43; 602/54
[58] Field of Search ................................ 602/48, 41, 58

[56] References Cited

U.S. PATENT DOCUMENTS 5,681,579 10/1997 Freeman .

*Primary Examiner*—John G. Weiss
*Assistant Examiner*—Kelan Hart
*Attorney, Agent, or Firm*—Marvin S. Aronoff

[57] ABSTRACT

A wound dressing that efficiently absorbs fluid from fluid exuding wounds and can easily be released from the wound without disrupting the wound surface and a process for its manufacture is provided. The dressing comprises a layer of film bonded to a fibrous absorbent web containing a mixture of a particulate superabsorbent and a hydrocolloid. The fibrous absorbent web has a glazed exposed surface wherein the fibers comprising the glazed exposed surface are substantially fused to each other. The glazed exposed surface has a multiplicity of particles comprising a mixture of an adhesive and a hydrocolloid distributed throughout and adherent to the surface. Preferably about 25% to about 50% of the surface is left uncovered by particles comprising the adhesive and the hydrocolloid to enable more efficient transfer of wound exudate into the fibrous absorbent web while the hydrocolloid contained in the particles of adhesive facilitates release of the dressing from the wound without disrupting the surface. A selvage encompasses the wound dressing, with the selvage comprising fibers of the fibrous absorbent web that are substantially fused to each other and to the layer of film bonded to the fibrous absorbent web.

19 Claims, 2 Drawing Sheets

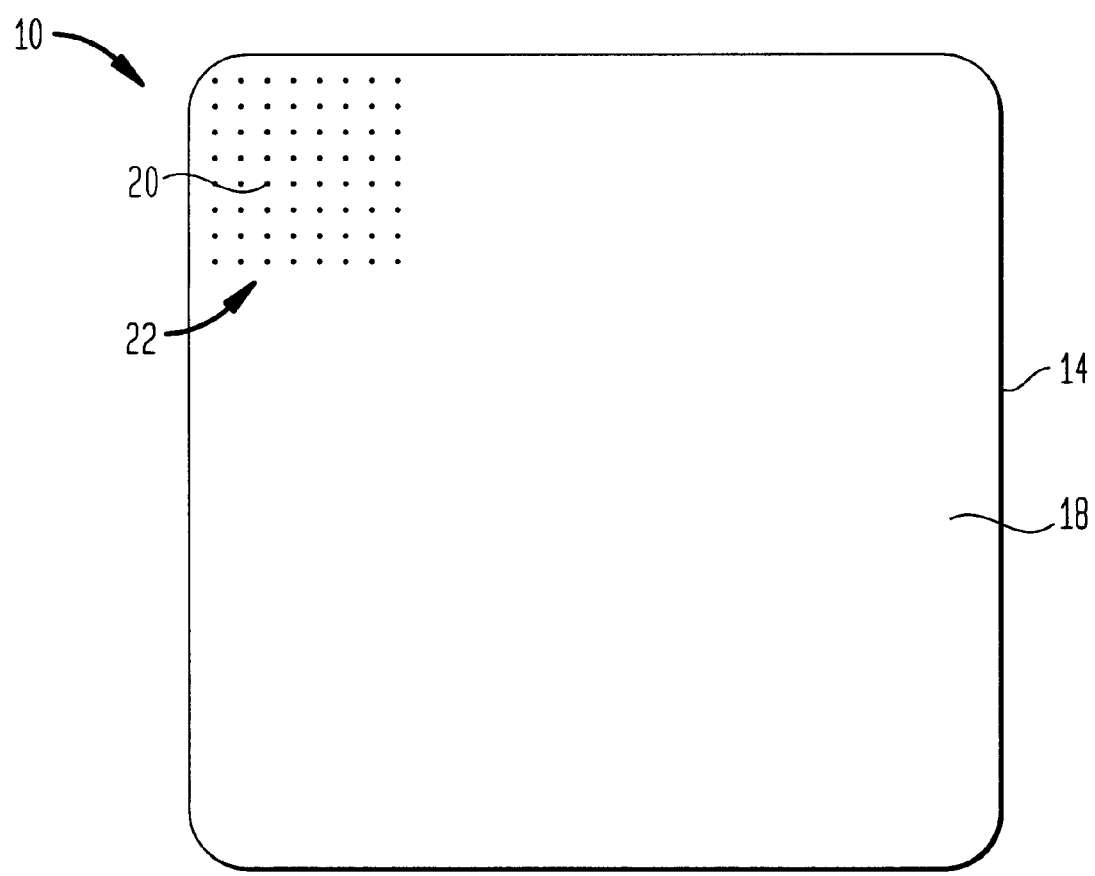

RELEASABLE WOUND DRESSING FOR EFFICIENT REMOVAL OF EXUDED FLUID

BACKGROUND OF THE INVENTION

This invention deals with improvements in occlusive and semi-occlusive dressings that promote healing of ulcerated tissue and other lesions in the skin.

Of the many dressings currently on the market that use hydrocolloids most are based principally on polymers such as polyisobutylene (PIB) alone or in combination with other polymers such as styrene—isoprene copolymers which are loaded with various gums natural origin or synthetic substances such as superabsorbents to create wet tack and to give a degree of absorption.

Although some of the currently available hydrocolloid based dressings have proved effective in clinical settings they suffer from a number of defects. These defects include messiness resulting from saturation with and overflow of wound exudate and difficulty in cleaning up, difficulty in removal from the wound area and leakage of wound exudate when first applied. A further difficulty with some of these hydrocolloid dressings is the generation of unpleasant odors. Yet another difficulty is the generation of allergic reactions due to the presence of allergens. For leg ulcer patients allergic reactions can be a serious problem as they have often been sensitized by exposure to many medicaments over many years.

A fundamental difficulty with dressings based on PIB alone or in combination with styrene—isoprene copolymers that contributes to, or causes the aforementioned difficulties, is the inability of such wound dressings to absorb fluids exuded from wounds such as leg ulcers at a rate commensurate with the rate at which the body produces such fluids.

There is a need for a hydrocolloid wound dressing that is so designed and constructed that it can absorb wound exudate at a rate more nearly commensurate with the rate at which the body produces such fluids. Such a wound dressing would eliminate or ameliorate problems with current hydrocolloid wound dressings such as messiness, saturation and overflow, difficulty in removal and cleanup and odor generation. There is a further need for a hydrocolloid wound dressing that does not produce allergic reactions, particularly in patients that have been sensitized.

BRIEF DESCRIPTION OF THE INVENTION

The present invention is directed to meeting the foregoing needs by providing a hydrocolloid wound dressing comprising a backing film and a fibrous absorbent web containing a mixture of hydrocolloids and superabsorbents overlying the backing film. The exposed or outer surface of the fibrous absorbent web is a smooth glazed surface comprising the fibers of the fibrous absorbent web. A material comprising a hydrocolloid is printed in a discontinuous pattern, such as dots, on the glazed surface of the wound dressing leaving a sufficient area of the glazed surface exposed to permit rapid transfer of wound exudate into the interior of the absorbent web when the wound dressing is placed in contact with a wound. The structure of the wound dressing of the present invention provides a highly efficient means for removal of fluid exuding from the surface of wounds while allowing the dressing to be easily removed without disrupting the healing process.

BRIEF DESCRIPTION OF THE DRAWINGS

FIG. 4 is a view of the glazed surface of the underside of the wound dressing of the present invention that depicts a pattern of hydrocolloid on a portion of the glazed surface.

DESCRIPTION OF THE PREFERRED EMBODIMENTS

Figure 1:
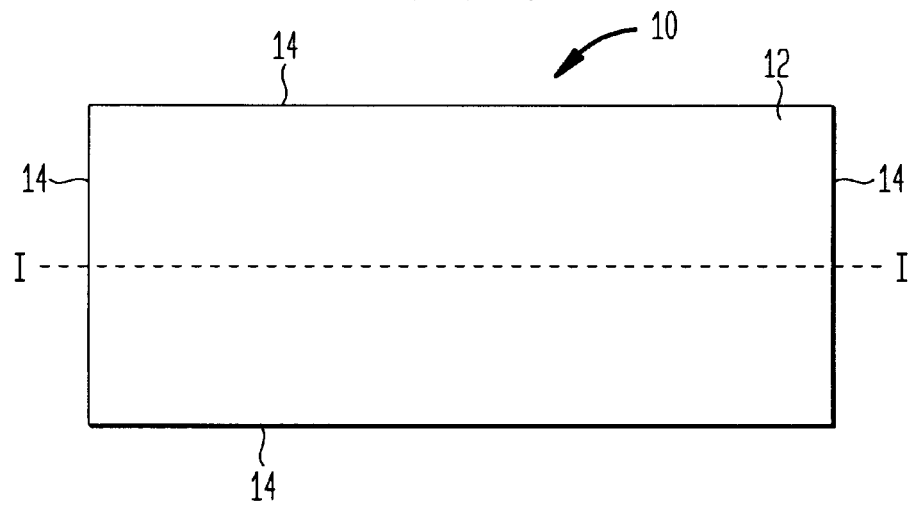
FIG. 1 is a top view of an embodiment of the wound dressing of the present invention.

FIG. 1 is a top view of an embodiment of wound dressing 10 of the present invention depicting an outer film layer or polymeric cover layer 12 that generally is not in contact with the skin when wound dressing 10 is used. The wound dressing is sealed at the edges via seals 14 which are essentially selvages formed by fusing the fibers of the fibrous webbing 16 (FIG. 2) to each other and to outer film layer 12. Outer film layer 12 is generally occlusive and impervious to fluid transmission. Outer film layer 12 has a degree of moisture vapor transmission as reflected by its moisture vapor transmission rate property (MVTR). Units for MVTR are grams per square meter per 24 hours ($g/M^2/24$ hrs) measured at 90% RH in accord with a standard protocol, for example, ASTM E96-66 which is herein incorporated by reference. For applications where low levels of moisture are required, outer film layer 12 is comprised of films having relatively low MVTR's and for applications requiring relative high levels of moisture evaporation outer film layer 12 is comprised of films having relatively high MVTR's. In general, outer layer 12 may be comprised of films having MVTR's from about 0.5 to about 4000 as required by the specific application, with films having MVTR's from about 20 to about 1000 preferred and with films having MVTR's from about 80 to about 800 more preferred. Examples of films suitable for outer film layer 12 include films and laminated films comprised of: polyurethanes; polyolefins including but not limited to polethylenes (PE), polypropylenes (PP), and copolymers of olefins with other unsaturated monomers bearing oxygen, nitrogen or halogen containing functional groups such as ethylene vinyl acetate (EVA); sarans including, vinylidene chloride polymers and copolymers with vinyl chloride; polyvinyl chloride (PVC) polymers and copolymers; methyl acrylate and methyl methacrylate copolymers; nylons; polyesters; and copolymers and physical blends thereof. Soft films are generally preferred for outer layer 12 for most wound dressing applications although in some instances stiffer films may be desirable to help restrict motion where the wound occurs at or near a joint. Films comprising polyurethanes and polyurethane copolymers, EVA copolymers, polyethylene and polypropylene are examples of preferred films useful for outer layer 12. Films having coatings derived from saran, coatings based on $SiO_2$, metallized coatings and other barrier coatings may also be used alone or in combination with uncoated films to form outer film layer 12 having an appropriate MVTR. In addition, laminated film structures may also be used to form outer film layer 12 having an appropriate MVTR. Other examples of films, particularly soft films, may be found in U.S. Pat. No. 5,681,579 which is herein incorporated by reference. Generally film thicknesses from about 0.5 mil to about 3 mil are preferred.

Figure 2:
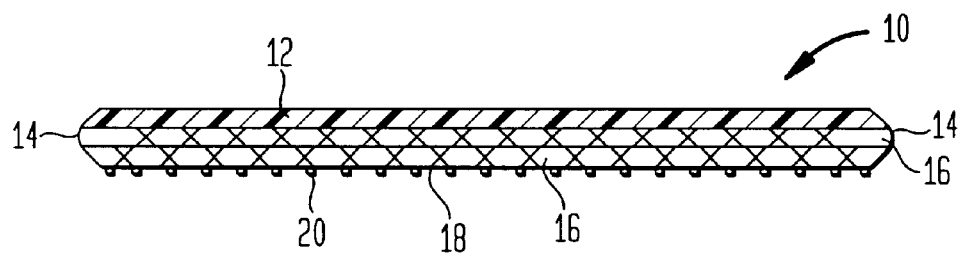
FIG. 2 is a cross-sectional view along line I—I of the embodiment of the wound dressing depicted in FIG. 1.

FIG. 2 is a cross-sectional view of wound dressing 10 along line I—I of FIG. 1. Wound dressing 10 comprises an outer film layer 12, a central layer or core comprising an absorbent material, typically a fibrous web, 16 containing a superabsorbent intermixed with a hydrocolloid. Fibrous web 16 is generally comprised of thermoplastic fibers or fibers that soften sufficiently under the application of heat and pressure so that they adhere or fuse to each other. Web 16 may also be comprised of composite fibers where one component imparts thermoplasticity or the ability to adhere to itself under the application of heat and or pressure as is known in the art. In addition, fibers that are generally not thermoplastic, such as cotton, cellulose derivatives and wool, that have been coated or treated with thermoplastic or thermoadhesive substances known in the art so that they have the capability to adhere or fuse to each other under the application of heat and pressure may comprise web 16. Fibrous web 16 is preferably comprised of thermoplastic fibers such as polypropylene, polyethylene, polyesters, nylons, with polypropylene being most preferred due to its low cost and availability.

Figure 3:
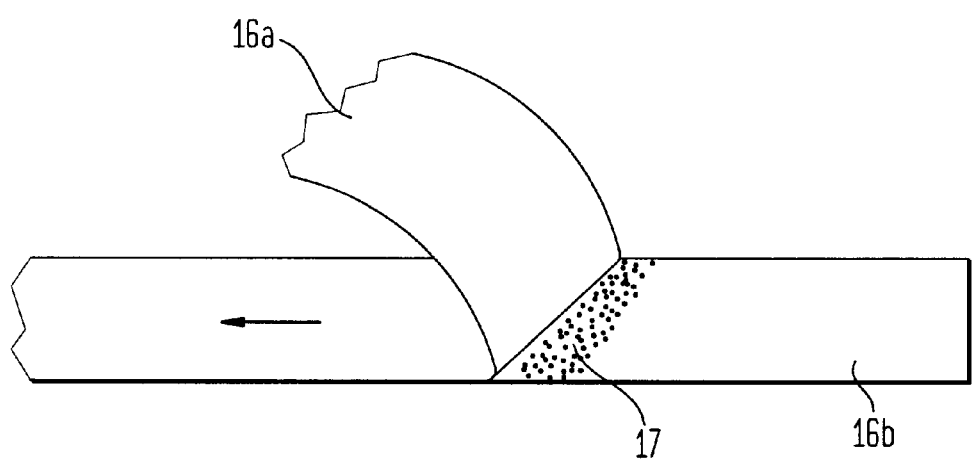
FIG. 3 is a schematic depiction of the formation of the fibrous absorbent web containing a mixture of hydrocolloids and superabsorbents.

FIG. 3 schematically depicts formation of fibrous absorbent layer 16 comprising an absorbent material, typically a fibrous web, that contains a superabsorbent intermixed with a hydrocolloid. In a typical process, a superabsorbent and hydrocolloid mixture 17 is deposited on a layer of a fibrous web 16a which is then covered by a second layer of fibrous web 16b and sent through calendering rolls in the direction indicated by the arrow. The resultant web is then needle punched to form a more cohesive fibrous web structure 16 containing hydrocolloid and superabsorbent. In some instances fibrous web 16a and fibrous web 16b may differ in composition. For example, fibrous web 16 may be formed from a layer of fibrous web 16a comprised of thermoplastic fibers such as polypropylene and a layer of fibrous web 16b comprised of a non-thermoplastic cellulosic fiber such as cotton. In such cases glazed undersurface 18 is formed on thermoplastic layer 16a of fibrous web 16.

The previously incorporated U.S. Pat. No. 5,681,579 provides details on processes for the formation of superabsorbent containing webs as well as superabsorbent compositions and hydrocolloid compositions useful in forming superabsorbent and hydrocolloid mixture 17. Other absorbent materials that may comprise mixture 17 are disclosed in U.S. Pat. No. 5,681,579, however superabsorbents are preferred for their high capacity. Other hydrocolloids useful in forming mixture 17 are disclosed in U.S. Pat. Nos. 3,339, 546 to Chen; U.S. Pat. No. 4,393,080 to Pawelchak et al; and U.S. Pat. No. 4,538,603 to Pawelchak et al which are all incorporated herein by reference. The superabsorbents and hydrocolloid formulations described in the previously incorporated U.S. Pat. No. 5,681,579 may likewise comprise hydrocolloid superabsorbent mixture 17 of the present invention.

The hydrocolloid and superabsorbent components of mixture 17 may be mixed or blended prior to deposition on web using standard equipment and procedures known in the art or they may be separately deposited on web 16 to form mixture 17 in situ.

The exposed surface 18 of fibrous web 16 is a generally smooth, glazed surface in which the fibers on the exposed surface of web 16 are generally fused as a result of exposure to conditions that cause a degree of localized melting and softening. Generally, as is known in the art, momentary contact of a webbing comprised of thermoplastic fibers, or fibers having a thermoplastic coating, with rolls heated to temperatures between about 300° F. to about 450° F. will result in glazing of the fibers that come into direct contact with the heated rolls. Fusion of the fibers in web 16 also occurs, to some extent, among the fibers of web 16 that are immediately adjacent to surface 18. The range of temperatures useful in glazing the surface of needle punched absorbent web 16 is dependent on the polymer stick temperature and the melting point of the polymeric composition comprising the fibers of web 16. Typically, roll temperatures for glazing needle punched absorbent web 16 will be at least the temperature at which the particular fibers comprising the web tend to soften and adhere to each other.

In a typical process, needle punched absorbent web 16 is laminated or bonded to outer film layer 12 by adhesive, thermal or ultrasonic means and methods known and practiced in the art so that glazed surface 18 remains exposed. In some cases it may be more convenient or economical to glaze both surfaces of needle punched web 16. In such cases, lamination of absorbent web 16 to outer film layer 12 will cover one glazed surface leaving the other glazed surface 18 exposed.

Particles of adhesive 20 are distributed on, and adhere to glazed surface 18. FIG. 4 depicts the glazed undersurface 18, which is generally the surface in contact with or proximate to the wound, of an embodiment of wound dressing 10. A portion of glazed surface 18 is covered with a pattern 22 of adhesive particles or dots 20. Pattern 22 is a representative portion of the pattern covering undersurface 18. Pattern 22 typically substantially covers glazed undersurface 18. Typically, pattern 22 or other patterns are deposited on surface 18 by printing and transfer processes known in the art. More random patterns of adhesive particles may be deposited on surface 18 from suspensions of the adhesive using coating roll technology known in the art. A key factor in depositing the particles comprising hydrocolloid and adhesive on surface 18 is to leave sufficient space within the pattern for wound fluid to reach absorbent web 16 containing hydrocolloids and superabsorbents. After deposition of the particles, about 15% to about 60% of undersurface 18 is left uncovered, or conversely the particles comprising an adhesive and hydrocolloid are distributed over and adherent to, about 40% to about 85% of undersurface 18. Preferably about 25% to about 50% of undersurface 18 is left uncovered by particles comprising adhesive corresponding to about 50% to about 75% covered by adhesive particles, to enable more efficient transfer of wound exudate into fibrous absorbent web 16. While the open pattern comprising a multiplicity of dots 20 facilitates transfer of exudate away from the wound surface, hydrocolloid contained in dots or particles 20 facilitates release of the dressing from the wound without disrupting the surface.

In another embodiment of wound dressing 10 of the present invention, the surface of needle punched absorbent web 16 is not glazed and particles or dots comprising a hydrocolloid formulation are deposited on the exposed surface of absorbent web 16.

The particles or dots comprising pattern 22 generally have a diameter of about 1/16 inch to about 3/32 inch and extend about 1 mil to about 2 mils away from undersurface 18. The hydrocolloid dots preferably comprise a mixture of commercially available acrylic pressure sensitive adhesive commonly used for medical applications and hydrocolloids such as those described earlier for use in forming mixture 17 of FIG. 3. However, any of the medical grade adhesives known in the art such as rubber based pressure sensitive adhesives may be used. Other adhesives and adhesive formulations useful for the formulation comprising skin contacting particle or dots 20 are given in the previously incorporated U.S. Pat. No. 5,681,579. The mixture of hydrocolloid and acrylic pressure sensitive adhesive has relatively low tack. Hydrocolloids preferred for reducing the tack of commercial acrylic pressure sensitive adhesives used in medical applications are pectin, sodium methyl cellulose and mixtures thereof. Amounts of hydrocolloid effective in forming a low tack adhesive range from about 10% to about 50% of the total weight of the hydrocolloid acrylic pressure sensitive adhesive mixture. At the lower end of the range the adhesive mixture has the highest tack while at the higher end of the range tack is lowest. For wound dressings to be used on highly sensitive skin, and to avoid damage to the healing wound on removal, lower tack formulations are generally preferred.

The device of the present invention may be formed by processes and techniques known and practiced in the art. For example, Freeman, in the previously incorporated U.S. Pat. No. 5,681,579, describes lamination and sealing processes involving fibrous webs that are loaded with components such as superabsorbents and hydrocolloids. Typically, an embodiment comprising polyethylene film, fibrous polypropylene web and a mixture of superabsorbent and hydrocolloid can be formed in the following steps:

a) distributing or loading the superabsorbent—hydrocolloid mixture onto a first layer of fibrous polypropylene web,
 b) laying down a second layer of fibrous polypropylene web on top of the first layer so that the superabsorbent—hydrocolloid mixture is contained within the two layers of web,
 c) calendering or otherwise compressing the web,
 d) needle punching the web to unite the layers,
 e) glazing at least one side of the web,
 f) laminating a layer of polyethylene film to the top of the fibrous web using adhesive, thermal or ultrasonic bonding means to form a laminate having a top layer of polyethylene film bonded to the fibrous web containing a mixture of superabsorbent and hydrocolloid with a glazed side of the fibrous web remaining exposed,
 g) depositing particles of a hydrocolloid containing adhesive on about 40% to about 85% of the glazed surface,
 h) calendering the laminate structure of step g),
 i) cutting the laminate into desired lengths and widths and shapes and simultaneously or subsequently fusing the fibers of the fibrous web at the edges to themselves and to the top film layer by ultrasonic or other means known in the art to form a selvage.

In the case of wound dressings comprised of polypropylene or polyethylene webs and polyethylene or polypropylene films ultrasonic sealing is preferred. In this case, the final web is cut into suitable shapes and sizes and the edges sealed by means of ultrasonic techniques. Other techniques such as adhesive means or conventional heat sealing and others known in the art may be preferable, as is known in the art, depending on the specific combinations of materials used. The wound dressings of the present invention can be cut and sealed and also shaped and formed by any means known in the art to form shapes and sizes individualized to the appropriate area of the skin to be treated, for example, limbs.

As will be evident to those skilled in the art, the steps in the foregoing process may be varied to achieve the same final wound dressing structure. For example, in some instance it may be technically advantageous to interchange steps e) and f) so that lamination of outer film layer 12 to fibrous web 16 precedes formation of glazed surface 18 on fibrous web 16. In addition, as is known in the art, it may be advantageous, with at least some compositions of the adhesive forming dots 20, to interleave a release layer on top of the adhesive dots to prevent roll blocking or adhesion to packaging material.

The wound dressing of the present invention may be rendered sterile as necessary by conventional means known in the art including heat, gamma radiation and treatment with ethylene oxide.

The wound dressing of the present invention may be applied to exuding wounds such as leg ulcers, decubitus ulcers and burns and others. The wound dressing is typically applied to the wound so that the particles 20 comprising a hydrocolloid come into direct contact with the exuding surface of the wound. In this manner, wound exudate is efficiently channeled through the open areas between the particles and into absorbent web 16. The wound dressing of the present invention may be covered by tapes, bandages and other appliances to secure it in place over the wound or as a component of other therapeutic treatment. In those cases where the particles 20 are comprised of an adhesive—hydrocolloid formulation having relatively high tack, adhesion of the wound dressing to the wound and the area around the wound may be sufficiently strong to secure it to the wound without additional means. The wound dressing of the present invention may be of such dimension and shape as required to cover the wound and secure it to the body. The wound dressing of the present invention may be changed as necessary to retain the wound surface in a sufficiently dry condition. However, both the quantity of hydrocolloid—superabsorbent mixture 17 within absorbent web 16 and the relative quantities of hydrocolloid and superabsorbent within mixture 17 may be adjusted along a continuum to provide relatively high or relatively low capacity for wound exudate. For a given wound, embodiments of the wound dressing of the present invention having higher capacities for absorption of wound exudate will need to be changed less frequently than embodiments with lower capacity. Embodiments with lower capacities for absorption of wound exudate may be applied in situations where rapid drying of the wound should be avoided.

The structure of the wound dressing of the present invention provides a highly efficient means for removal of fluid exuding from the surface of wounds while allowing the dressing to be easily removed or released from the wound without disrupting the healing process. Although the present invention has been described in considerable detail with reference to certain preferred versions thereof, other versions are possible. Therefore, the spirit and scope of the appended claims should not be limited to the description of the preferred versions contained herein.

What is claimed is:

1. A wound dressing for the absorption of fluid from fluid exuding wounds comprising:
 a polymeric cover layer, with the cover layer bonded to a fibrous absorbent web, with the fibrous absorbent web containing;
  a mixture of a particulate superabsorbent and a hydrocolloid; and
 with the fibrous absorbent web having a glazed exposed surface wherein fibers comprising the glazed exposed surface are substantially fused to each other and with the glazed exposed surface having distributed thereon and adherent thereto a multiplicity of particles comprising;
  a mixture of an adhesive and a hydrocolloid; and
 a selvage that encompasses the wound dressing, with the selvage comprising fibers of the fibrous absorbent web that are substantially fused to each other and to the cover layer bonded to the fibrous absorbent web.

2. The wound dressing of claim 1 wherein the cover layer comprises a polymeric film having a composition selected from the group consisting of polyurethanes, polyolefins, ethylene vinyl acetate polymers, vinylidene chloride polymers and copolymers, polyvinylchloride polymers and copolymers, methyl acrylate and methyl methacrylate copolymers, and copolymers and physical blends and laminates thereof.

3. The wound dressing of claim 2 wherein the fibers comprising the fibrous absorbent web are selected from the group consisting of thermoplastic fibers, composite fibers having a thermoplastic component, fibers coated with thermoplastic and mixtures thereof with non-thermoplastic fibers.

4. The wound dressing of claim 3 wherein the film comprising the cover layer is selected from the group consisting of polyethylene films, polypropylene films, polyurethane films, ethylenevinylacetate copolymer films, polyvinylidenechloride polymer films and laminates thereof.

5. The wound dressing of claim 4 wherein the fibers comprising the fibrous absorbent web are selected from the group consisting of polypropylene fibers, polyethylene fibers, polyester fibers, nylon fibers and blends and mixtures thereof.

6. The wound dressing of claim 5 wherein the particles comprising a mixture of an adhesive and a hydrocolloid are distributed over and adherent to about 40 percent to about 85 percent of the exposed glazed surface.

7. The wound dressing of claim 6 wherein the mixture of an adhesive and a hydrocolloid comprises an acrylic pressure sensitive adhesive and a hydrocolloid selected from the group consisting of pectin, sodium methyl cellulose and mixtures thereof.

8. The wound dressing of claim 1 wherein the cover layer has a moisture vapor transmission rate of less than about 4000 grams per square meter per 24 hours.

9. The wound dressing of claim 8 wherein the cover layer has a moisture vapor transmission rate of about 20 grams per square meter per 24 hours to about 1000 grams per square meter per 24 hours.

10. The wound dressing of claim 9 wherein the cover layer has a moisture vapor transmission rate of about 80 grams per square meter per 24 hours to about 800 grams per square meter per 24 hours.

11. A method for producing a releasable wound dressing for the efficient removal of exuded fluid from a wound surface comprising the steps of:

a) providing a first and a second layer of a web comprising a fibrous thermoplastic;

b) forming a mixture of a superabsorbent and a hydrocolloid;

c) distributing the mixture onto the first layer of the fibrous web;

d) laying down the second layer of fibrous web on top of the first layer so that the mixture is contained within the two layers of fibrous web;

e) compressing the two layers of web containing the mixture;

f) uniting the two layers of web by means that produce a substantially cohesive web;

g) glazing at least one side of the united web to form at least one outer layer substantially comprised of fused fibers;

h) providing a polymeric film and bonding a layer of the polymeric film to a side of the glazed web to form a laminate having an exposed glazed side;

I) providing an adhesive that contains hydrocolloid and distributing and adhering a multiplicity of adhesive particles onto about 40 percent to about 85 percent of the exposed glazed surface of the laminate;

j) cutting the laminate into segments having a selvage encompassing each segment by means that substantially simultaneously fuse the fibers of the fibrous web at a cut edge to themselves and to the polymeric film bonded to the glazed web.

12. The method of claim 11 wherein in step a) the first and the second layer of the web comprising a fibrous thermoplastic are selected from the group consisting of polypropylene fibers, polyethylene fibers, polyester fibers, nylon fibers and blends and mixtures thereof.

13. The method of claim 12 wherein in step f) the means is needle punching.

14. The method of claim 13 wherein in step g) the web is glazed at a temperature of about 300° F. to about 450° F.

15. The method of claim 14 wherein in step h) the polymeric film is selected from the group consisting of polyethylene films, polypropylene films, polyurethane films, ethylenevinylacetate copolymer films, polyvinylidenechloride polymer films and laminates thereof.

16. The method of claim 15 wherein in step h) the polymeric film is ultrasonically bonded to the side of the glazed web.

17. The method of claim 16 wherein in step I) the adhesive is distributed by pattern printing.

18. The method of claim 17 wherein step I) further comprises calendering the pattern printed laminate.

19. The method of claim 18 wherein in step j) the laminate is cut ultrasonically.

* * * * *